United States Patent [19]

Guigues et al.

[11] 4,155,747
[45] May 22, 1979

[54] DERIVATIVES OF TETRAHYDRO-1,3,5-OXADIAZIN-4-ONE AND HERBICIDAL COMPOSITIONS CONTAINING THESE DERIVATIVES

[75] Inventors: François Guigues, Rillieux; Gilles Peris-y-Saborit, Lyon, both of France

[73] Assignee: Philagro, Lyon, France

[21] Appl. No.: 851,795

[22] Filed: Nov. 15, 1977

[30] Foreign Application Priority Data

Dec. 6, 1976 [FR] France ................. 76 37543

[51] Int. Cl.$^2$ .................. A01N 9/20; C07D 273/04
[52] U.S. Cl. ........................... 71/92; 544/68
[58] Field of Search .................. 544/68; 71/92

[56] References Cited
FOREIGN PATENT DOCUMENTS 1450485  4/1965  France ........................ 544/68

Primary Examiner—John D. Randolph
Attorney, Agent, or Firm—Browdy & Neimark

[57] ABSTRACT

Selective herbicides useful for the destruction of weeds in crops such as wheat, maize (corn), rice, cotton, groundnuts and soya, correspond to the following formula:

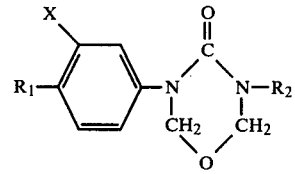

in which $R_1$ is an alkyl of 2-4 carbons, preferably isopropyl, $R_2$ is an alkyl of 1-4 carbons, preferably methyl, and X is halogen, preferably chloro or fluoro.

9 Claims, No Drawings

DERIVATIVES OF TETRAHYDRO-1,3,5-OXADIAZIN-4-ONE AND HERBICIDAL COMPOSITIONS CONTAINING THESE DERIVATIVES

The present invention relates to new derivatives of tetrahydro-1,3,5-oxadiazin-4-one, which correspond to the general formula

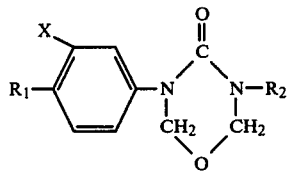

formula 1 in which $R_1$ represents an alkyl radical containing from 2 to 4 carbon atoms, X represents a halogen atom and $R_2$ represents an alkyl radical containing from 1 to 4 carbon atoms.

The invention furthermore relates to the preparation of these compounds. Finally, it relates to the herbicidal compositions which contain, as the active material, at least one compound according to formula 1, as well as to the use of these compositions for the selective destruction of weeds in crops such as wheat, maize, rice, cotton, groundnuts and soya.

A plurality of derivatives of 3-phenyl-tetrahydro-1,3,5-oxadiazin-4-one have already been described, and amongst them some have been described because of their herbicidal properties.

Thus, French Pat. No. 1,450,485 describes compounds corresponding to the general formula

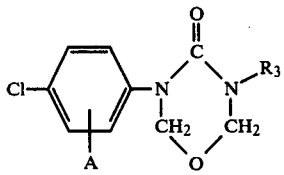

formula 2 in which A represents a hydrogen atom, a methyl group or a chlorine atom and $R_3$ represents an alkyl radical containing from 1 to 8 carbon atoms. The herbicidal activity of the compounds described in this patent is often satisfactory, but their toleration by major crops, such as wheat, maize, soya and cotton, is generally inadequate at the customary use doses and it is thus not possible to use them without risk for these crops.

In fact, in order that a selective herbicide shall be usable in practice for the destruction of weeds in a given crop, it is essential that it should, at its use dose, simultaneously exhibit:

On the one hand, the highest possible herbicidal activity against the largest possible number of weeds present in this crop, and on the other hand, the highest possible toleration by this crop.

The compounds according to the present invention conform to this double requirement. At their customary use doses, they are well tolerated by crops such as wheat, maize, rice, soya, cotton and groundnuts, in pre-emergence treatment of the latter. At the same doses, they exhibit a very high herbicidal activity against the principal weeds, including both graminaceous weeds and dicotyledonous weeds, present in these crops.

They can also be used by the post-emergence method for the destruction of weeds in wheat and maize.

Particularly valuable results are obtained with the compounds according to the invention which correspond to the general formula

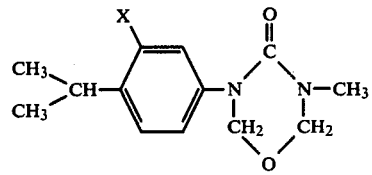

formula 3 in which X has the same meaning as in formula 1 and preferably represents a chlorine or fluorine atom.

The compounds according to the invention are prepared by reacting a N-phenyl urea derivative with formaldehyde or with a compound which liberates formaldehyde, such as polyoxymethylene or paraformaldehyde, in accordance with the following equation:

(reaction A)

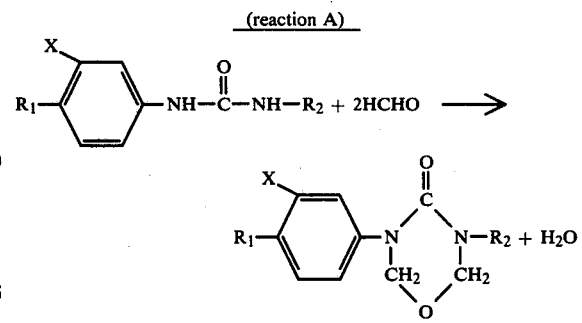

in which $R_1$, $R_2$ and X have the same meaning as in formula 1.

According to a first process, the reaction A is carried out in accordance with a known method described in French Pat. No. 1,542,912. For this, urea is reacted with paraformaldehyde or polyoxymethylene in solution in an inert organic solvent at a temperature of between 20° and 150° C. in the presence of an acid catalyst such as sulphuric acid or p-toluenesulphonic acid. The organic solvent used is a polar solvent such as dioxane, dimethylsulphoxide or dimethylformamide, or a solvent mixture containing both an aromatic solvent and a polar solvent. The reaction is carried out by heating the reaction mixture to the reflux temperature until water is no longer formed. Preferably, the reaction is carried out in a benzene/dioxane solvent mixture in the presence of para-toluenesulphonic acid, at a temperature of between 20° and 120° C.

According to a second process which is in itself new, the reaction A is carried out in an inert aromatic solvent such as toluene or benzene, in the presence of an acid catalyst system comprising on the one half dimethylformamide and on the other hand a strong acid such as para-toluenesulphonic acid or sulphuric acid, at a temperature of between 70° and 90° C. In the acid catalyst system, the molar ratio of dimethylformamide/strong acid is between 0.1 and 2. The overall molar ratio of catalyst system/urea starting material is between 0.01 and 1 and preferably between 0.05 and 0.8. Working up in accordance with these conditions, the reaction has taken place with a satisfactory yield after about 15 minutes against more than one hour when using the first of the processes described in the present application.

The urea used as the starting material in each of the two processes described is prepared according to one of the conventional methods of preparation of N-phenylureas, for example by reacting a primary amin with a phenylisocyanate.

The examples which follow are given by way of nonlimiting examples, in order to illustrate the invention.

EXAMPLE 1: Preparation of 3-(3-chloro-4-isopropyl-phenyl)-5-methyl-tetrahydro-1,3,5-oxadiazin-4-one N-(3-Chloro-4-isopropyl-phenyl)-N',N'-dimethylurea (22.65 g.=0.1 mol) is dissolved in a solvent mixture comprising dioxane (50 cc.) and benzene (80 cc.). After adding p-toluenesulphonic acid (1 g.) and polyoxymethylene (8.1 g.), the solution is heated under reflux for 1 hour in a flask equipped with a Dean and Stark apparatus with a reflux condenser. 3.7 cc. of aqueous phase are collected.

The reaction mixture is evaporated to dryness, the residue is taken up in benzene and the solution is washed twice with 2 N HCl (40 cc.) and then with a saturated sodium bicarbonate solution (50 cc.). After drying over MgSO$_4$, and evaporating the benzene, 3-(3-chloro-4-isopropyl-phenyl)-5-methyl-tetrahydro-1,3,5-oxadiazin-4-one is recovered in the form of an oil which crystallises very easily. After recrystallisation from hexane, this compound melts at 63.0° C.

| % | Percentage analysis | | |
|---|---|---|---|
| | C | H | N |
| Calculated | 58.10 | 6.33 | 10.43 |
| Found | 58.32 | 6.37 | 10.42 |

EXAMPLE 2

Following the method of Example 1 but starting from N-(3-bromo-4-isopropyl-phenyl)-N'-methylurea, 3-(3-bromo-4-isopropyl-phenyl)-5-methyl-tetrahydro-1,3,5-oxadiazin-4-one (boiling point under 0.003 mm Hg: 184° C.) was prepared.

| % | Percentage analysis | | |
|---|---|---|---|
| | C | H | N |
| Calculated | 49.88 | 5.43 | 8.95 |
| Found | 50.33 | 5.48 | 8.59 |

EXAMPLE 3: Preparation of 3-(3-fluoro-4-isopropyl-phenyl)-5-methyl-1,3,5-oxadiazin-4-one according to the second of the processes described in the present application N-(3-Fluoro-4-isopropyl-phenyl)-N'-methyl-urea (one mol=210 g.) and polyoxymethylene (1 mol=90 g.) are dissolved in toluene (800 cc.) in the presence of para-toluenesulphonic acid (0.3 mol=51.6 g.) as a catalyst and of dimethylformamide (0.3 mol=22 g.), and the mixture is heated for 15 minutes at 80° C. After having washed the solution with water and then concentrated it, 3-(3-fluoro-4-isopropyl-phenyl)-5-methyltetrahydro-1,3,5-oxadiazin-4-one is obtained in the form of an oil which is purified by dissolving in hot hexane and recrystallising.

Melting point: 45° C. Yield: 82%.

| % | Percentage analysis for $C_{13}H_{17}N_2O_2F$ | | |
|---|---|---|---|
| | C | H | N |
| Calculated | 61.90 | 6.75 | 11.11 |
| Found | 62.08 | 6.88 | 10.72 |

EXAMPLE 4: Herbicidal action in the pre-emergence treatment of crops in a greenhouse A number of seeds chosen in accordance with the plant species to be sown and the size of the seed is sown in 9×9×9 cm. pots filled with light agricultural soil. The seeds are then covered with a layer of soil about half a centimetre thick.

After moistening the soil, the pots are treated by spraying with an amount of liquor per pot, at the dose of active material in question, corresponding to a volume of 500 l/ha.

The liquor is prepared by diluting with water an emulsifiable concentrate having the following composition by weight:
active material to be tested—20%
wetting and deflocculating agent—10%
cyclohexanone (solvent)—70%
to the desired dilution, containing the active material at the dose in question. The tests were carried out at doses of active material ranging from 1 kg/ha to 8 kg/ha.

The treated pots are then placed in troughs intended to receive the watering water by sub-irrigation, and kept for 35 days at ambient temperature under 70% relative humidity.

After 35 days, the degree of destruction of the plant species in question is determined relative to a reference sample treated under the same conditions with a dispersion which does not contain active material.

In the table which follows, we have shown, for each of the compounds tested:

In the case of the crops the dose of active material, in kg/ha, which produces at most 20% destruction of the crop in question, and in the case of the weeds, the dose of active material which produces a percentage destruction of at least 90% of the weed in question.

In practice, a herbicidal product is the more valuable, the higher is the dose of this product which the crops withstand and the lower is the dose which is active against the weeds.

| | Compound of Ex. 1 | Compound of Ex. 2 | Compound of Ex. 3 |
|---|---|---|---|
| Crops | | | |
| Wheat (*Triticum vulgare*) | =8 | >8 | >8 |
| Maize (*Zea mays*) | >8 | >8 | >8 |
| Rice (*Oryza sativa*) | >8 | >8 | >8 |
| Cotton (*Gossypium hirsutum*) | >8 | >8 | >8 |
| Soya (*Glycine max*) | =8 | | >8 |
| Beans (*Phaseolus vulgaris*) | =4 | 8 | 2 |
| Graminaceous weeds | | | |
| Crabgrass (*Digitaria sanguinalis*) | =1 | =1 | <1 |
| Raygrass (*Lolium italicum*) | =2 | =3 | <1 |
| Foxtail (*Setaria faberi*) | =3 | =3 | 2 |
| Dicotyledonous weeds | | | |
| Goosefoot (*Chenopodium sp.*) | <1 | <1 | <1 |
| Nightshade (*Solanum nigrum*) | <1 | <1 | <1 |
| Mustard (*Sinapis alba*) | <1 | 6.5 | <1 |
| Chickweed (*Stellaria media*) | <1 | <1 | <1 |
| Yellow oxeye daisy (*Chrysanthemum* | =1 | 8 | <1 |

-continued

|  | Compound of Ex. 1 | Compound of Ex. 2 | Compound of Ex. 3 |
| --- | --- | --- | --- |
| segetum) |  |  |  |

EXAMPLE 5: Herbicidal action in post-emergence treatment of crops

For the post-emergence test, the composition to be tested is applied to the plants at the stage of two true leaves, the other test conditions being the same as in the preceding example.

For each of the compounds tested, the figures given in the table below indicate, as in Example 4:

In the case of the crops, the dose of active material, in kg/ha, which produces at most 20% destruction of the crop in question, and in the case of the weeds, the dose of active material, in kg/ha, which produces a percentage destruction of at least 90% of the weed in question.

|  | Compound of Ex. 1 | Compound of Ex. 2 | Compound of Ex. 3 |
| --- | --- | --- | --- |
| Crops |  |  |  |
| Wheat (*Triticum vulgare*) | =8 | =8 | 8 |
| Maize (*Zea mays*) | >8 | =5 | 8 |
| Gramineaceous weeds |  |  |  |
| Crabgrass (*Digitaria sanguinalis*) | <1 | 2 | <2 |
| Barnyard grass (*Echinochloa crus-galli*) | <1 | <1 | 1 |
| Raygrass (*Lolium italicum*) | <1 | <1 | 1 |
| Foxtail (*Setaria faberi*) | <1 | 1.5 | <2 |
| Dicotyledonous weeds |  |  |  |
| Goosefoot (*Chenopodium sp.*) | <1 | <1 | <1 |
| Nightshade (*Sola-num nigrum*) | <1 | <1 | <1 |
| Mustard (*Sinapis alba*) | <1 | <1 | <1 |
| Chickweed (*Stellaria media*) | <1 | <1 | <1 |
| Yellow oxeye daisy (*Chrysanthemum segetum*) | 3.5 | 8 | 4 |

EXAMPLE 6: Comparative selectivity test on crops, in the pre-emergence treatment of the latter This test compares the selectivity on crops of wheat (*Triticum vulgare*), maize (*Zea mays*), rice (*Oryza sativa*), cotton (*Gossypium barbadense*), groundnuts (*Arachis hypogea*) and soya (*Glycine max*), on the one hand of the compounds described in Examples 1 and 3 of the present application and, on the other hand, of the following compounds:

3-(3,4-Dichloro-phenyl)-5-methyl-tetrahydro-1,3,5-oxadiazin-4-one: compound A.

3-(4-Chloro-phenyl)-5-methyl-tetrahydro-1,3,5-oxadiazin-4-one: compound B.

These compounds A and B are respectively the compounds described in Examples 1 and 3 of French Pat. No. 1,450,485 cited above.

The method used is that described in Example 4 of the present application, but employing compositions in the form of wettable powders, respectively containing (by weight):

material to be tested—20%
filler (kaolin)—69%
anti-caking silica—5%
deflocculating agent (calcium lignosulphate)—5%
wetting agent (Na isopropylnaphthalenesulphonate)—1%

These selectivity tests are carried out at doses of active material ranging from 1 to 8 kg/ha.

The figures shown in the table below indicate the degrees of destruction of the plant species treated under the conditions indicated, relative to the untreated comparison plants. A degree of 100 indicates complete destruction of the species in question. In order to be acceptable in the case of crops, the degree of destruction must not exceed about 20% and preferably be less than 10%.

| Crops | Doses in kg/ha | Compound of Ex. 1 | Compound of Ex. 3 | Compound A | Compound B |
| --- | --- | --- | --- | --- | --- |
| Wheat | 1 | 0 | 0 | 5 | 0 |
|  | 4 | 0 | 0 | 80 | 25 |
|  | 8 | 10 | 0 | 100 | 85 |
| Maize | 1 | 0 | 0 | 0 | 0 |
|  | 4 | 0 | 0 | 80 | 20 |
|  | 8 | 0 | 0 | 100 | 60 |
| Rice | 1 | 0 | 0 | 0 | 0 |
|  | 4 | 10 | 0 | 60 | 0 |
|  | 8 | 15 | 0 | 80 | 15 |
| Cotton | 1 | 0 | 0 | 15 | 0 |
|  | 4 | 0 | 0 | 100 | 0 |
|  | 8 | 0 | 0 | 100 | 15 |
| Groundnuts | 1 | 0 | 0 | 0 | 0 |
|  | 4 | 0 | 0 | 0 | 0 |
|  | 8 | 0 | 0 | 25 | 5 |
| Soya | 1 | 0 | 0 | 100 | 0 |
|  | 4 | 0 | 0 | 100 | 50 |
|  | 8 | 20 | 0 | 100 | 60 |

This comparison shows that for doses ranging from 1 to 8 kg/ha, the compounds of Examples 1 to 3 in general exhibit much better toleration by the crops in question than do the comparison compounds.

EXAMPLE 7—Comparative test of the herbicidal activity on weeds, in the pre-emergence treatment of the latter This test relates to the same compounds as in the previous example, which are tested in accordance with the method described in Example 4. For each of the compounds tested, the composition used is that described in Example 6. The comparison was carried out for doses of active material ranging from 0.25 to 2 kg/ha. The figures shown in the table below indicate, for each of the compounds tested, at a given dose, the percentage destruction of the plant species treated, relative to the untreated comparison plants. A degree of 100 indicates complete destruction of the species in question and hence a complete herbicidal activity.

|  | Dose in kg/ha | Compound of Ex. 1 | Compound of Ex. 3 | Compound A | Compound B |
| --- | --- | --- | --- | --- | --- |
| Wild oats (*Avena fatua*) | 1 | 0 | 0 | 0 | 0 |
|  | 2 | 0 | 0 | 15 | 0 |
| Crabgrass (*Digitaria sanguinalis*) | 0.25 | 5 | 20 | 70 | 0 |
|  | 1 | 80 | 100 | 100 | 100 |
|  | 1 | 100 | 100 | 100 | 100 |
| Barnyard grass (*Echinochloa crus-galli*) | 0.25 | 0 | 0 | 0 | 0 |
|  | 1 | 50 | 85 | 90 | 0 |
|  | 2 | 95 | 100 | 100 | 25 |
| Raygrass (*Lolium multiflorum*) | 0.25 | 20 | 10 | 60 | 0 |
|  | 1 | 80 | 90 | 90 | 80 |
|  | 2 | 90 | 95 | 100 | 90 |
| Foxtail (*Setaria faberii*) | 0.25 | 0 | 0 | 0 | 0 |
|  | 1 | 0 | 60 | 90 | 30 |

-continued

| | Dose in kg/ha | Compound of Ex. 1 | Compound of Ex. 3 | Compound A | Compound B |
|---|---|---|---|---|---|
| | 2 | 30 | 95 | 100 | 98 |
| Goosefoot | 0.25 | 80 | 80 | 70 | 80 |
| (*Chenopodium album*) | 1 | 100 | 100 | 90 | 100 |
| | 2 | 100 | 100 | 100 | 100 |
| Yellow oxeye daisy | 0.25 | 0 | 0 | 80 | 60 |
| (*Chrysanthemum* | 1 | 60 | 95 | 100 | 100 |
| *segetum*) | 2 | 100 | 100 | 100 | 100 |
| Nightshade | 0.25 | 80 | 80 | 80 | 0 |
| (*Solanum nigrum*) | 1 | 100 | 100 | 100 | 50 |
| | 2 | 100 | 100 | 100 | 80 |
| Mustard | 0.25 | 0 | 0 | 0 | 0 |
| (*Sinapis alba*) | 1 | 95 | 90 | 60 | 30 |
| | 2 | 100 | 100 | 95 | 80 |
| Chickweed | 0.25 | 80 | 80 | 80 | 30 |
| (*Stellaria media*) | 1 | 100 | 100 | 90 | 60 |
| | 2 | 100 | 100 | 100 | 80 |

The results described in Examples 6 and 7 show that the compounds of Examples 1 and 3 exhibit substantially the same herbicidal activity on the weeds in question as the comparison compounds A and B, but that they differ very markedly from the latter by much better selectivity towards the crops in question, and more particularly towards wheat, maize, cotton, groundnuts and soya. They can thus be used without risk for the destruction of weeds in these crops, at doses of active material ranging from 0.5 to 8 kg/ha and preferably of the order of 1 to 3 kg/ha.

For use in practice, the compounds according to the invention are rarely employed alone. Most frequently, they form part of formulations which in general comprise a carrier and/or a surface-active agent in addition to the active material according to the invention.

The term "carrier" in the sense of the present description denotes an organic or inorganic, natural or synthetic material with which the active material is associated in order to facilitate its application to the plant, to the seeds or to the soil, or to facilitate its transport or its handling. The carrier can be solid (clays, natural or synthetic silicates, resins, waxes, solid fertilisers and the like) or fluid (water, alcohols, ketones, petroleum fractions, chlorinated hydrocarbons and liquefied gases).

The surface-active agent can be an emulsifier, dispersing agent or wetting agent, and each of these can be ionic or non-ionic. As examples there may be mentioned salts of polyacrylic acids and of ligninsulphonic acids, and condensates of ethylene oxide with fatty alcohols, fatty acids or fatty amines.

The compositions according to the invention can be prepared in the form of wettable powders, dusting powders, granules, solutions, emulsifiable concentrates, emulsions, suspension concentrates and aerosols.

The wettable powders are usually prepared in such a way that they contain from 25 to 95% by weight of active material and they usually contain, in addition to a solid carrier, from 0 to 5% by weight of wetting agent and from 3 to 10% by weight of one or more stabilisers and/or other additives, such as penetrating agents, adhesives, anti-caking agents, dyestuffs and the like. By way of example, the following is the composition of a wettable powder.

active material (compound of Example 1)—50%
calcium lignosulphate (deflocculating agent)—5%
anionic wetting agent—1%
anti-caking silica—5%
kaolin (filler)—39%

The water-soluble powders are obtained by mixing from 20 to 95% by weight of active material, from 0 to 10% of an anti-caking extender and from 0 to 1% of a wetting agent, the remainder consisting of a water-soluble extender, principally a salt. The following is an example of a composition of a water-soluble powder:

active material (compound of Example 1)—70%
anionic wetting agent—0.5%
anti-caking silica—5%
sodium sulphate (soluble extender)—24.5%

The granules, intended to be put on the soil, are usually prepared in such a way that they have sizes of between 0.1 and 2 mm, and they can be manufactured by agglomeration or impregnation. In general, the granules contain from 0.5 to 25% of active material and from 0 to 10% by weight of additives such as stabilisers, slow-liberation modifiers, binders and solvents.

The emulsifiable concentrates which can be applied by spraying usually contain, in addition to the solvent and, where necessary, a co-solvent, from 10 to 50% by weight/volume of active material and from 2 to 20% by weight/volume of appropriate additives, such as stabilisers, penetrating agents, corrosion inhibitors and adhesive dyestuffs.

By way of example, the following is a composition of an emulsifiable concentrate, the amounts being expressed in g/liter:

active material (compound of Example 1)—400 g/l
alkali metal dodecylbenzenesulphonate—24 g/l
nonylphenol reacted with 10 molecules of ethylene oxide—16 g/l
cyclohexanone—200 g/l
aromatic solvent—q.s.p.—1 liter.

The suspension concentrates, which can also be applied by spraying, are prepared so that a stable fluid product which does not settle out is obtained, and they usually contain from 10 to 75% by weight of active material, from 0.5 to 15% by weight of surface-active agents, from 0.1 to 10% by weight of thixotropic agents, from 0 to 10% by weight of appropriate additives, such as anti-foaming agents, corrosion inhibitors, stabilisers, penetrating agents and adhesives and, as a carrier, water or an organic liquid in which the active material is substantially insoluble; certain organic solid materials or inorganic salts can be dissolved in the carrier to assist in preventing sedimentation or to act as anti-freeze agents for the water.

Aqueous dispersions and aqueous emulsions, for example compositions obtained by diluting a wettable powder or an emulsifiable concentrate according to the invention with water, fall within the general scope of the present invention. The emulsions can be of the water-in-oil type or of the oil-in-water type and they can have a thick consistency such as that of a "mayonnaise".

The compositions according to the invention can contain other ingredients, for example protective colloids, adhesives or thickeners, thixotropic agents, stabilisers or sequestering agents as well as other known active materials possessing pesticidal properties, in particular possessing insecticidal or fungicidal properties.

We claim:

1. A compound of the formula:

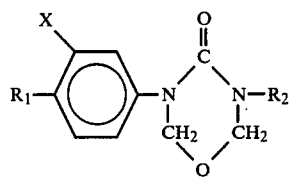

in which:

$R_1$ represents an alkyl radical containing from 2 to 4 carbon atoms,

X represents a halogen atom and $R_2$ represents an alkyl radical containing from 1 to 4 carbon atoms.

2. Compound according to claim 1, of the formula

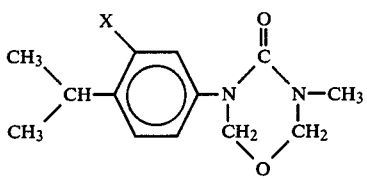

in which X has the same meaning as in claim 1.

3. Compound according to claim 1, which is 3-(3-chloro-4-isopropyl-phenyl)-5-methyltetrahydro-1,3,5-oxadiazin-4-one.

4. Compound according to claim 1, which is 3-(3-fluoro-4-isopropyl-phenyl)-5-methyltetrahydro-1,3,5-oxadiazin-4-one.

5. Process for the selective destruction of weeds in crops of wheat, maize, rice, cotton, soya and groundnuts, comprising applying to the ground in which seeds of said crops have been planted or in which said crops have sprouted an amount sufficient to destroy weeds without destruction of said crop of the compound of claim 1.

6. Process according to claim 5, wherein the treatment of crops is carried out by the pre-emergence method and in that the dose of active material applied to between 0.5 and 8 kg/ha.

7. Process for the preparation of the compound according to claim 1, wherein formaldehyde or a compound which liberates formaldehyde is reacted with a N-phenyl urea derivative of the formula:

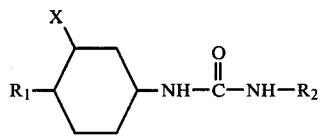

in which $R_1$, X and $R_2$ have the same meaning as in claim 1, in an inert aromatic organic solvent of toluene or benzene, in the presence of an acid catalyst mixture including dimethyl formamide at a temperature of between 70° and 90° C., said acid catalyst comprising a mixture of said dimethyl formamide with a strong acid in a molar ratio of acid to dimethyl formamide of between 0.1 and 2, the molar ratio of said acid catalyst mixture to the N,N'-disubstituted phenyl urea being between 0.01 and 1.

8. An herbicidal composition for the selective destruction of weeds in crops of wheat, maize, rice, soya, cotton and groundnuts, comprising an inert carrier suitable for agricultural use and an amount sufficient of a compound in accordance with claim 1 to destroy weeds without destruction of said crop and within the range of 0.5–95% by weight of said composition.

9. Composition according to claim 8, further comprising a surface-active agent.

* * * * *

UNITED STATES PATENT AND TRADEMARK OFFICE
CERTIFICATE OF CORRECTION

PATENT NO. : 4,155,747
DATED : May 22, 1979
INVENTOR(S) : GUIGES et al.

It is certified that error appears in the above—identified patent and that said Letters Patent are hereby corrected as shown below:

The structural formula of claim 7 should read:

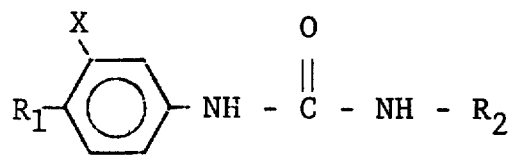

Signed and Sealed this

Ninth Day of October 1979

[SEAL]

Attest:

RUTH C. MASON
Attesting Officer

LUTRELLE F. PARKER
Acting Commissioner of Patents and Trademarks